(12) United States Patent
Gurney (10) Patent No.: US 10,453,564 B2
(45) Date of Patent: Oct. 22, 2019

(54) DEVICE AND METHOD FOR CROSS-REFERENCING

(71) Applicant: LEICA BIOSYSTEMS MELBOURNE PTY LTD, Mount Waverly, Victoria (AU)

(72) Inventor: Phillip Clyde Roberts Gurney, Victoria (AU)

(73) Assignee: LEICA BIOSYSTEMS MELBOURNE PTY LTD, Mount Waverly, Victoria (AU)

(*) Notice: Subject to any disclaimer, the term of this patent is extended or adjusted under 35 U.S.C. 154(b) by 475 days.

(21) Appl. No.: 15/395,004

(22) Filed: Dec. 30, 2016

(65) Prior Publication Data

US 2017/0140107 A1   May 18, 2017

Related U.S. Application Data

(63) Continuation of application No. 13/721,591, filed on Dec. 20, 2012, now abandoned, which is a
(Continued)

(30) Foreign Application Priority Data

Apr. 11, 2006   (AU) .................................. 2006901906

(51) Int. Cl.
*G16H 10/60* (2018.01)
*G01N 1/36* (2006.01)
(Continued)

(52) U.S. Cl.
CPC ............... *G16H 10/60* (2018.01); *G01N 1/36* (2013.01); *G01N 35/00732* (2013.01);
(Continued)

(58) Field of Classification Search
CPC .... G16H 10/60; G01N 1/60; G01N 35/00732; G06Q 50/24; G06Q 10/063114; G06Q 50/22; G06K 7/1413; G06K 7/1417
(Continued)

(56) References Cited

U.S. PATENT DOCUMENTS 3,536,550 A * 10/1970 Von Hofe .............. B31D 1/021
101/181
4,893,424 A    1/1990 McLean
(Continued)

FOREIGN PATENT DOCUMENTS

CA    2 232 468 A1    11/1999
WO    03040697 A1     5/2003
(Continued)

OTHER PUBLICATIONS

General Data Company, Case Study: Massachusetts General Hospital: The FedEx Of Pathology Labs, 2005, General Data Company, pp. 1-6 (Year: 2005).*
(Continued)

*Primary Examiner* — Joy Chng
(74) *Attorney, Agent, or Firm* — Sughrue Mion, PLLC (57) ABSTRACT

A sample, embedded in a paraffin block, is placed on a tissue cassette which carries a label which may be a bar code. When the sample is processed, the cassette is given to a microtome operator who scans the label. Scanning causes information to be displayed on a screen and the operator verifies that what is on the screen matches what was on the label. The paraffin block is then placed in a microtome chuck and sections are cut from the block. A number of slide labels related to the cassette label are printed for the sections. If the operator does not verify that the information displayed on the screen matches the information on the cassette label and/or does not place the paraffin block in the microtome
(Continued)

chuck within an allocated time interval after scanning the cassette label, dispensing and labeling of slides and/or operation of the microtome is prevented.

23 Claims, 7 Drawing Sheets

Related U.S. Application Data continuation of application No. 12/296,830, filed as application No. PCT/AU2007/000475 on Apr. 11, 2007, now Pat. No. 9,691,043.

(60) Provisional application No. 60/744,632, filed on Apr. 11, 2006.

(51) Int. Cl.
| | | |
|---|---|---|
| *G01N 35/00* | (2006.01) | |
| *G06Q 50/24* | (2012.01) | |
| *G06Q 10/06* | (2012.01) | |
| *G06Q 50/22* | (2018.01) | |
| *G06K 7/14* | (2006.01) | |

(52) U.S. Cl.
CPC ......... *G06K 7/1413* (2013.01); *G06K 7/1417* (2013.01); *G06Q 10/063114* (2013.01); *G06Q 50/22* (2013.01); *G06Q 50/24* (2013.01)

(58) Field of Classification Search
USPC .......................................................... 705/2–3
See application file for complete search history.

(56) References Cited

U.S. PATENT DOCUMENTS

| | | | | |
|---|---|---|---|---|
| 5,960,085 | A | * | 9/1999 | de la Huerga ........ A61J 1/1437 |
| | | | | 340/5.61 |
| 5,963,368 | A | * | 10/1999 | Domanik ............. G02B 21/365 |
| | | | | 356/72 |
| 6,045,759 | A | | 4/2000 | Ford et al. |
| 7,867,442 | B2 | | 1/2011 | Graupner et al. |
| 8,178,536 | B2 | | 5/2012 | Graupner et al. |
| 8,676,509 | B2 | | 3/2014 | De La Torre-Bueno |
| 2004/0108225 | A1 | | 6/2004 | Friedlander et al. |
| 2004/0114714 | A1 | * | 6/2004 | Minyard .............. A61B 5/0002 |
| | | | | 378/37 |
| 2004/0253662 | A1 | * | 12/2004 | Heid ........................ G01N 1/06 |
| | | | | 435/40.52 |
| 2005/0037406 | A1 | | 2/2005 | Torre-Bueno et al. |
| 2005/0059155 | A1 | * | 3/2005 | Graupner ................ B01L 3/545 |
| | | | | 436/43 |
| 2005/0090017 | A1 | | 4/2005 | Morales |
| 2006/0236703 | A1 | | 10/2006 | Rada |
| 2008/0220460 | A1 | | 9/2008 | Kawaminami et al. |
| 2009/0214088 | A1 | | 8/2009 | Sorenson et al. |

FOREIGN PATENT DOCUMENTS

| | | | | |
|---|---|---|---|---|
| WO | 2004113911 | A1 | | 12/2004 |
| WO | 2005031312 | A1 | | 4/2005 |
| WO | WO 2005/031312 | | * | 4/2005 ............... B01L 3/16 |

OTHER PUBLICATIONS

Notice of Allowance dated Feb. 23, 2017 issued in U.S. Appl. No. 12/296,830.
Case Study: Massachusetts General Hospital: The FedEx Of Pathology Labs, 2005, General Data Company, pp. 1-6.
Case Study: Massachusetts General Hospital: The Fed Ex of Pathology Labs (online), (Retrieved on Jan. 8, 2007). Retrieved from thr Internet URL://w.w.w.general-data.com/industry/Healthcare/stainershield/Stainer%20Shield%20Case%20Study%20-%20MGH.pdf.
Moher, R., et al., "Labeling and Tracking Preventing Errors in the Lab", (online), Barcoding and RFID, Sep./Oct. 2005 (Retrieved on Jan. 8, 2007). Retrieved from the Internet URL: http://www.psqh.com/sepoct05/barcodingrfid4.html.
Supplementary European Search Report for Application No. EP 07 71 8722, dated Nov. 8, 2011.

* cited by examiner

DEVICE AND METHOD FOR CROSS-REFERENCING

CROSS REFERENCE TO RELATED APPLICATIONS

This application is a continuation of U.S. application Ser. No. 13/721,591 filed Dec. 20, 2012, which is a continuation of U.S. application Ser. No. 12/296,830 filed Apr. 17, 2009, which is a national stage entry of PCT/AU2007/000475 filed on Apr. 11, 2007, which claims priority to Australian Patent Application No. 2006901906 filed Apr. 11, 2006, and the benefit of priority from U.S. Provisional Patent Application No. 60/744,632 filed Apr. 11, 2006.

FIELD OF INVENTION

The present invention relates to a system, device and method for cross-referencing sample holders on which tissue samples are to be disposed and a support of an associated tissue sample.

BACKGROUND

Accurate identification of samples within a laboratory is vital to correctly linking a diagnosis to a patient. The correlation of tissue sample sections, such as thin tissue sections on a microscope slide, with the tissue sample support, such as a paraffin-embedded tissue block from which the sections were obtained, is critical to accurate analysis and diagnosis.

Typically, the workflow within a histology laboratory is as follows:

A biopsy sample is delivered in a container by courier from a doctor's surgery. The sample container is given an accession ID relevant to the laboratory, and is then passed on to the cut-up (grossing) area. Here, the sample is removed from the container, and cut up to excise pieces of interest. The pieces of interest are placed into one or more tissue cassettes, which are uniquely labelled to link them to the accession ID. Any remaining specimen tissue is returned to the initial container for storage.

The tissue cassettes are batched into a collection basket, and when sufficient are available they are placed into a tissue processor where the tissue pieces are infiltrated with wax to support the tissues and allow cutting of thin sections (e.g. 2-10 microns) at the microtome. The collection basket is transferred to the embedding work-station. Here, working on a single cassette at a time to minimize errors, tissue pieces are removed from the cassettes and placed into a mould. Molten wax is poured into the mould, and the tissue cassette base, which carries the identification information, is placed on the top of the mould. When the mould is cooled, a tissue block is produced in which the paraffin holds together the cassette base and the embedded pieces, allowing for identification of the tissues embedded in the paraffin block.

The embedded tissue block is passed to the microtome operator, who places identification information relating to the tissue block onto one or more microscope slides, as necessary, and then places the block into the microtome chuck. Thin sections (e.g. 2-10 microns) are cut from the block and transferred onto the identified microscope slides, traditionally by floating the paraffin sections onto a water-bath and then scooping them up with the microscope slide.

Slides are then batched into a drying rack, transferred into a staining rack and placed into a staining mechanism, where features of the tissues are stained in various colours. Once stained, the slides have a thin glass coverslip applied to protect the tissue and improve the optical properties of the slide for viewing in a microscope. At this point, the slides are ready to pass to a pathologist for diagnosis.

However, due to the possibility of identification errors in the above process, two further time-consuming steps are required. Firstly, a machine printed label is applied. It is usual that the initial identification markings placed on the slide by the microtome operator are handwritten in pencil. Pencil markings are used because they are resistant to the chemicals used in slide staining. Unfortunately, hand-written pencil markings are often hard to read and are not smudgeproof, and so after staining it is common to apply a machine-printed label to the slide to provide an easily read and smudgeproof identification. The application of a label at this step allows for human error in identifying the sample.

Secondly, slides and tissue blocks are collated to reduce identification errors. In this step, a human operator examines each and every slide and tissue block to verify that the tissue on the slide does indeed come from the tissue block that the label identifies it as coming from, and that the tissue in the block is of the correct type and size as expected. This collation step is labour intensive and provides significant delays in diagnosis. Finally, after collation, tissue blocks are filed and slides can be distributed to pathologists for diagnosis.

In general, errors may arise anywhere where a sample is moved from one container to another, where sections are taken from the sample, or when a sample is re-labelled. As can be seen, in the above processing workflow five separate identification steps, and a checking step are required;

1. Tissue samples arrive in containers and an accession ID is attached to the container.
2. The tissue is removed from the container, out up and the pieces are placed into cassettes—the cassette IDs are required to identify not only the sample from which the pieces come, but also the part of the sample to which they relate.
3. Processed tissues pieces are embedded into a paraffin tissue block, and the cassette ID is transferred to the tissue block by attaching the base of the cassette to the paraffin mould.
4. At the microtome, sections are cut from the samples and are placed onto microscope slides. The slides need to be marked in such a way as to identify the sample from which they came, usually by copying the cassette identifying marks onto the slide in pencil by hand. Multiple cassettes may be used per sample, and multiple slides can be required per cassette.
5. After staining, the hand-written slides are re-labelled with machine-printed labels.
6. A final collation step is required to ensure that the stained tissues on the slides, and the embedded tissues in the tissue block, match with the accessioned tissue sample.

Identification errors may occur at any one of these steps.

Furthermore, a consequence of the error-prone nature of current slide identification practices is that slide identification is not guaranteed until after staining—pre-stained slides contain sections that are so thin as to be optically transparent, and so features required for identification cannot yet be seen. Therefore collation is necessarily done after staining.

Automation of processes in a histology laboratory is seen as beneficial to improving quality and reducing turn around time, and can be assisted by automatic identification of the slide, e.g. using barcoding. Using current identification practices however, it is not possible to ensure error-free processing of slides based on machine-readable identification. Identification errors can only be picked up after staining has occurred, and correction of these errors requires time-consuming and costly re-testing, and involves the use of additional sample tissue. In many cases, this additional sample tissue may not be available.

A number of practices have evolved over the years to address the issue of cross-referencing. These practices include use of paper-based systems to identify cassette contents at the microtome, wherein a file of papers detailing the samples are passed along with the cassette and slide. These paper-based systems are generally not used, as transfer of paper records is clumsy, requires duplicate copies, and requires complex choices about workflow, such as whether the paper follows the cassettes, slides, both or neither. Paper-based systems also require additional desk space as well as the potential problem of paper records getting covered in paraffin and/or chemicals.

A major source of cross-referencing errors in the present process is slide identification. Currently, slide labels are predominantly hand-written, with the microtome operator transcribing the cassette identification information by hand to the slide. This is a time-intensive task with significant potential for human error. Handwriting requires handling of slides, which is especially undesirable as it may transfer skin cells to the slide surface. Additionally, handwriting clearly does not allow for machine-readable information to be created, and is thus not amenable to automatic identification of the slide.

A number of variations on the above standard workflow have evolved to address some of the shortcomings of hand-written labels. One such method, with a similar workflow to handwriting of slides, is to print sticky labels (using, for example, a thermal transfer printer) and hand-apply these labels to the slides. The labels can either be printed at the time of placing the sample on the slide or, alternatively, labels can be printed in batches beforehand. Application of labels is a time-consuming process that still requires handling of the slides, as no automatic label applicator yet exists that is used at a microtome station. Additionally, hand-application of labels is prone to the same human-error as hand-writing of slides, in that the human operator can mislabel slides.

Printers have been designed that are capable of printing directly onto slides using chemical resistant, smudgeproof inks. Such printers are expensive and bulky, and are not designed for, or suitable for, use at the microtome station. As a lab cannot generally afford more than one, they are used for printing large batches of slides. Similarly, label printers are capable of printing large batches of labels.

Another alternative workflow to that outlined above for handwriting is to use a printer to pre-print batches of slides or labels, arid distribute these slides, labels or pre-labelled slides together with the tissue blocks to the microtome operators. While this batch pre-printing process is common, it requires an additional time consuming and error-prone process of sorting marked slides or labels and allocating them, together with the tissue blocks, to the microtome operator. Furthermore, when using batch-pre-printing processes it is impossible to guarantee that the correct number of slides/labels are produced. This is because changes to the number of slides required can be made in the grossing (cut-up), embedding, and sectioning (microtome) stages of histology processing. This leads to both wastage of slides and labels that have been unnecessarily printed, and also to wasted time where the microtome operator must either hand-write additional slides, or print further slides on the batch printer.

It can be seen that there are problems with all of the above workflows. To date, no complete automated solution to the problem of cross-referencing of tissue holders and tissue supports has been developed, and no known process provides an automated identification prior to staining.

The present invention is directed to overcoming or at least alleviating the problems associated with the prior art.

SUMMARY

In a first aspect, the present invention provides a method for allocating identification information to a tissue holder, the method comprising:

identifying information of a tissue support with a device;

providing data on a display related to the identified tissue support;

verifying, within an allocated time interval after identification of the tissue support at the device, that the identifying information of the tissue support correlates with the data provided by the display, and preventing application of the identification information to the tissue holder, halting operation of a sectioning station to which the tissue support has been applied, or preventing the application of the identification information to the tissue holder and halting operation of the sectioning station, if the correlation of the identifying information of the tissue support with the data provided by the display is not verified within the allocated time interval after identification of the tissue support at the device.

In a preferred embodiment, the method according to the first aspect further provides that applying the identified tissue support to the sectioning station within the allocated time interval verifies that the identifying information of the tissue support correlates with the data provided by the display.

In a preferred embodiment, the method according to the first aspect further comprises applying the tissue support to the sectioning station.

In another embodiment, the method according to the first aspect of the invention further comprises applying information to the tissue holder that can be related back to at least a portion of the information of the tissue support.

In a second aspect, the present invention provides a method for allocating identification information to a tissue holder, the method comprising;

identifying information of a tissue support with a device;

applying identification information to a tissue holder that can be related back to at least a portion of the information of the tissue support;

communicating between the device and a sectioning station;

applying the tissue support to the sectioning station, and preventing application of the identification information to the tissue holder, halting operation of the sectioning station, or preventing the application of the identification information to the tissue holder and halting operation of the sectioning station, if the tissue support is not applied to the sectioning station within an allocated time interval after identification of the tissue support at the device.

In a preferred embodiment, the identification information applied to the tissue holder is substantially identical to the information of the tissue support.

In a preferred embodiment, applying the identified tissue support in the sectioning station within the allocated time interval initiates the device applying the identification information to a first tissue holder.

In a preferred embodiment, removal of a tissue holder from the device initiates the device applying the identification information to a further tissue holder, so long as the identified sample remains positioned in the sectioning station.

In a third aspect, the present invention provides a device for allocating identification information to a tissue holder, the device comprising:

a reader for reading an identifier which provides information associated with a tissue support for sectioning at a sectioning station;

a display for displaying data; and a transfer device for applying identification information to the tissue holder wherein the applied identification is related to the identifier of the tissue support; and a decision system for preventing the application of the identification information to the tissue holder, halting operation of the sectioning station, or preventing the application of the identification information to the tissue holder and halting operation of the sectioning station, if the information associated with the tissue support is not verified as correlating with displayed data related to the identified tissue support within an allocated time interval after identification of the tissue support at the device.

In a fourth aspect, the present invention provides a device for allocating identification information to a sample tissue holder, the device comprising:

a reader for reading an identifier which provides information associated with a tissue support for sectioning at a sectioning station;

a transfer device for applying identification information to a tissue holder wherein the applied identification is related to the identifier of the tissue support; and a decision system for preventing the application of the identification information to the tissue holder, halting operation of the sectioning station, or preventing the application of the identification information to the tissue holder and halting operation of the sectioning station, if the tissue support is not applied to the sectioning station within an allocated time interval after identification of the tissue support at the device.

In a preferred embodiment, the reader is integrated with the transfer device.

In one embodiment, the identification information applied to the tissue holder may be derived from the tissue support information. In a preferred embodiment, the identification information applied to the tissue holder is substantially identical to the tissue support information.

In a preferred embodiment, positioning the identified tissue support in the sectioning station within the allocated time interval initiates the device applying the identification information to the first tissue holder.

In a preferred embodiment, removal of an identified tissue holder from the device initiates the device applying the identification information to a further tissue holder, so long as the identified sample support remains positioned in the sectioning station.

In a further preferred embodiment, the identification information of the tissue support includes instructions for cutting and processing tissue samples that are to be disposed on the tissue holder.

In still a further preferred embodiment, the device is integrated with the sectioning station.

DETAILED DESCRIPTION OF PREFERRED EMBODIMENTS

Preferred embodiments of the present invention and their advantages may be understood by referring to FIGS. 1-7, like numerals being used for like corresponding parts in the various drawings.

The device and method described hereafter are preferred embodiments only, and the present invention is not limited to these preferred embodiments. The arrangement of elements of the device and method in FIGS. 1-7 in no way limits the present invention. It is within the contemplation of the present invention to arrange or modify elements of the device and method in accordance with other design requirements, such as, the amount of space available to accomplish the device and method of this invention.

In a preferred embodiment, the present invention provides an integrated system for producing tissue holders, such as histological slides.

Figure 1:
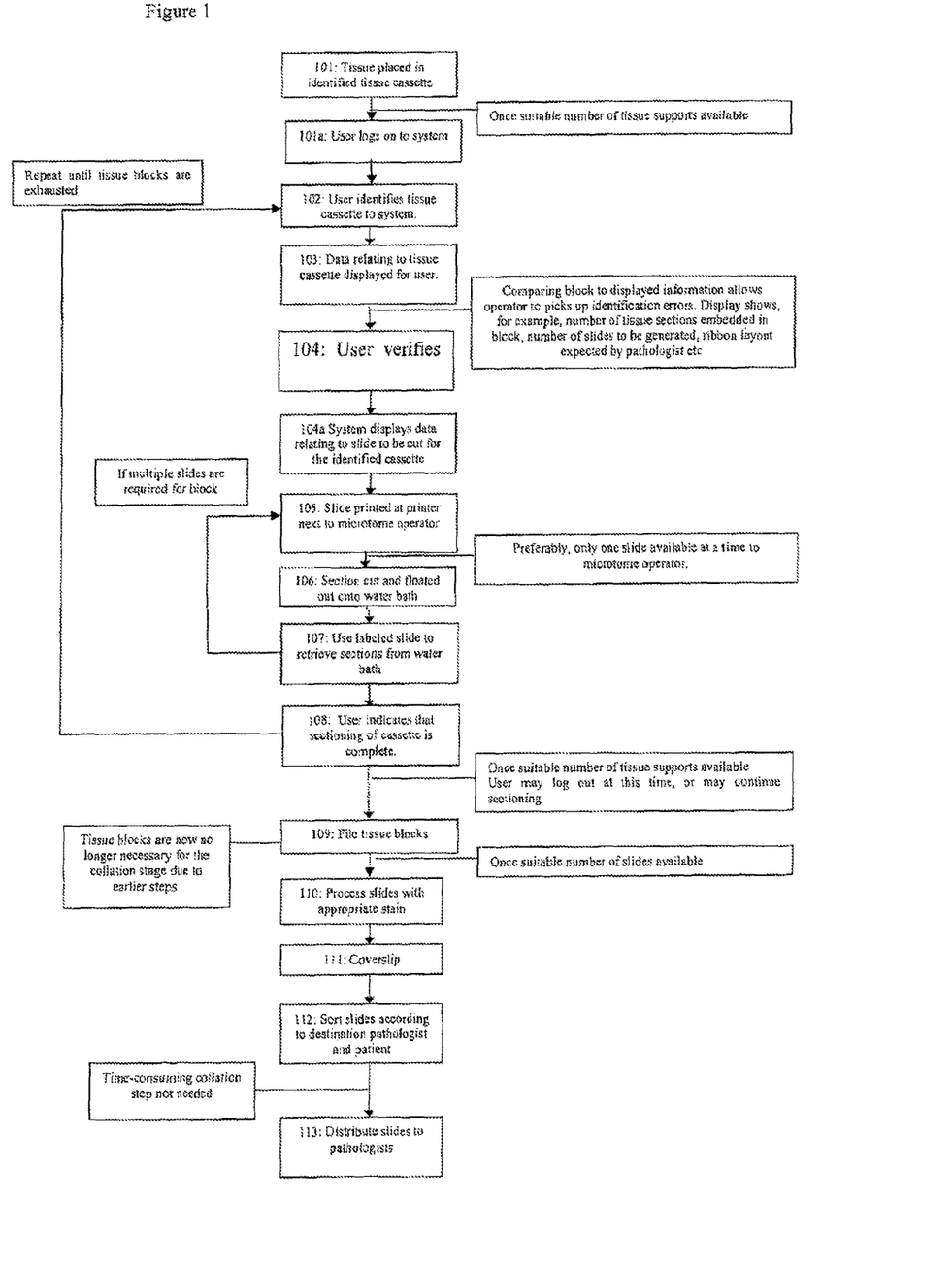
FIG. 1 is a flowchart of a method of automatically producing tissue holders according to one embodiment of the present invention.

FIG. 1 shows a flowchart of a method according to a preferred embodiment of the present invention, as related to a histology laboratory. First, in step 101 of FIG. 1, a processed tissue sample is placed in an identified tissue support to hold it for sectioning. Whilst a cassette is described as a preferred embodiment of a tissue support, and may be used interchangeably with the term tissue support, it will be appreciated that other tissue supports are within the scope of the present invention.

As used herein, the term "tissue sample" refers to a sample that is typically made up of a collection of biological cells and includes, but is not limited to, for example, biopsy samples, autopsy samples, surgical samples, cell smears, cell concentrates and cultured cells, bodily fluids, preparations for imprints, and preparations made from micro-organisms. The tissue sample generally includes any material for which microscopic examination of samples of the material prepared on microscope slides is desirable. Preferably, the tissue is human, animal or plant tissue. The tissue sample may be collected for diagnostic, research, teaching or other purposes.

Typically, tissue samples for histological examination are embedded in a support medium and moulded into standardized blocks. Paraffin wax is a known and commonly-used as a support medium, however it will be appreciated that other support media, including but not limited to, TissueTek O.C.T., manufactured by Sakura Finetek, ester, microcrystalline cellulose, bees wax, resins or polymers, such as methacrylates, may also be used as support media. Suitable resins and polymers, including Araldite 502 Kit, Eponate 12.™. Kit, and Glycol Methacrylate (GMA) Kit, are available from Ted Pella, Inc., Redding, Calif.

The prepared tissue support is labelled with an identifier (in histology this is usually marked on part of a tissue cassette base that is attached to and becomes part of the tissue support). Such identifiers include, but are not limited to, handwritten identifiers, printed text, a bar code (1, 2 or 3 dimensional), data glyphs, Optical Character Recognition (OCR) code, Radio Frequency Identification Technology (RFID) tags and e-ink.

Known input and labelling equipment may be used to input the information and to prepare the identifier on the tissue support. The technician preparing the tissue support may input a unique identifier, and additional information regarding the patient's name, type of sample (e.g., what organ the sample came from), the number of samples in the tissue support, the number of tissue supports relating to a particular accessioned sample, the number of slides that are to be made, the tests that are to be run, the stains which are to be performed or any other relevant information, and may print or affix a label containing some or all of the information on the front, or oh any non-working surface of the cassette. The information may be fixed to the tissue support in machine-readable form. For example, this information may be provided in a scannable bar code, data glyph, OCR font or RFID tag. Other forms of storage, such as magnetic or electronic media, may also be used. The identification information may include a code affixed to the tissue support that correlates with information about the sample that is stored external to the tissue support (for example in the LIS), and the code may facilitate access to the information.

In step 101a, the technician who will section the tissue support identifies themself and logs on to the sample identification system (for example by entering in an identifier, or by scanning an identity badge). Data relating to the user activity is stored in the system and allows for traceability and quality control data—for example the system can log which technician has worked on which tissue supports, and which workstation they used. The log-on system also allows a user hierarchy to be defined, such that some users are able to perform actions on the system (for example maintenance tasks, correcting data) that are not allowed by other users. The user remains logged on to the system until they log out, which may require an action on the part of the user, or may be automatic if the system has remained idle for a period of time. Preferably, no identified tissue holders can be printed by the system unless a user is logged in. A maintenance mode allows override of commands, and maintenance activities may be logged.

In step 102, the technician enters the tissue support identifier into the system. This can be a manual process, in which case the tissue support identifier may be entered into the system by the technician with, for example, a keypad or touch screen input device, however other input devices are within the scope of the present invention. Preferably the data entry is carried out by the user scanning in a machine-readable identifier on the tissue support. Scanning of information carried by the tissue support can be achieved using a suitable identification reader known in the art including, but not limited to bar-code (1, 2 or 3 dimensional), data glyphs, Optical Character Recognition (OCR), and RFID readers. The reader is preferably located in close proximity to the sectioning station, and may be integral with the sectioning station, or the printer if this is separate from the sectioning station.

Figure 6:
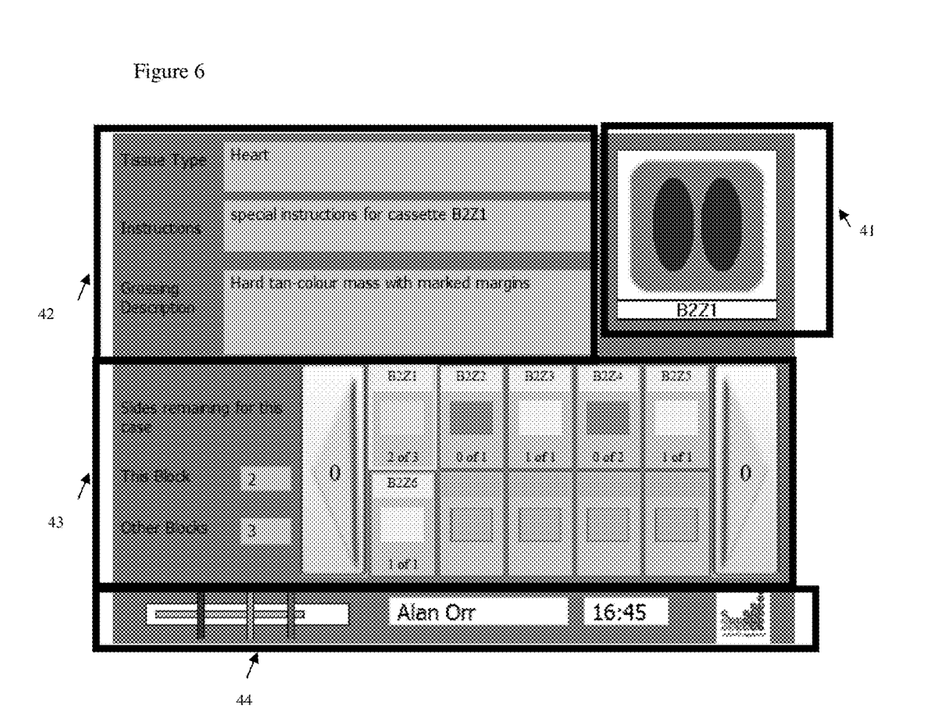
FIG. 6 shows an example of tissue support identification information that may be displayed to the user.

At step 103, after the tissue support ID has been entered, information related to the tissue support and the tissue sample it contains is displayed to the technician. The displayed information may simply indicate the tissue support identifier, but may further aid verification of the identity of the tissue holder and tissue sample by including additional information, for example the number and status of related tissue supports, the type and number of tissue pieces embedded in the tissue support, images and descriptions of the accessioned sample, patient data, instructions for cutting the tissue in the support, and any other relevant information. An example of the data that may be displayed at this step is shown in FIG. 6.

The additional displayed information may be accessed from a remote Laboratory Information System (LIS), or a local database, or may be encoded along with the tissue support ID (for example, the ID and information data may be encoded in a 2-D barcode or RFID chip). Some of the displayed information may be inferred from other available information, using laboratory rules. For example, the laboratory may have a rule that each time a liver biopsy is received, three slices are cut, with two being positioned on one microscope slide one above the other, and the third positioned on a second slide. If the tissue type is know, and the laboratory rules are encoded into the device, server or associated database, it is then possible for the device to infer that two slides are required each time a liver biopsy is encountered, and display relevant information about the cutting of the tissues.

In step 104, the user verifies the identity of the tissue support. This may be done manually, for example by pressing an appropriate button, key or area on a touch screen. Alternately, it may be automated by the use of a sensor identifying when the tissue support is loaded in a holding assembly, such as a microtome chuck. In some cases, both systems may be used. The tissue support may be secured in the holding assembly by several prongs, however other means of holding the tissue support, such as other mechanical means, a vacuum clamp or other such means may also be used. Whilst the preferred sectioning station described is a microtome, it will be appreciated that other devices including, but not limited to, cryostat microtomes, laser based cutting apparatus and touch preparation devices are within the scope of the present invention.

The sensor detecting the presence of the tissue support may be remote from, or incorporated into, the holding assembly, and may be in the form of an optical, mechanical, electronic, capacitative, inductive, magnetic (e.g. Hall effect), pressure, thermal, etc. switch that is activated when the cassette is in position and deactivated when it is removed. Other methods and devices for determining the presence of the cassette may also be used. The switch may sense the presence of the tissue support directly, or indirectly. For example, the switch may sense the position of a lever used to open and close the holder assembly, and the presence of a tissue support may be inferred if the lever is positioned away from its rest position for a period of time. Preferably, deactivation of the sensor prevents use of the microtome such that the microtome cannot operate in the absence of a tissue support, and/or prevents the printer from dispensing slides (see step 105). In one embodiment, the sensor is an optical imaging system.

In a preferred embodiment, when a tissue support is scanned at step 102, the decision-making system first verifies that there is no tissue support currently in the holding assembly. If a tissue support is present, the system flags an error and refuses to accept the scanned information.

The time interval between the technician identifying the tissue support to the system and then verifying the identity of the tissue support (for example by positioning the tissue support in the holding mechanism) is used to ensure accurate identification of the tissue support and the sample therein. If the verification does not occur within a predetermined time-frame, the processing of the tissue support and related tissue holders may be stopped automatically. This time limit assists in authenticating that the support identifier is correct, i.e. that it relates to the tissue support that has been positioned in the holding mechanism, and that the tissue support contains the correct sample tissue. For example, if the tissue support identifier is verified too quickly, it may be assumed that the user has not taken sufficient time to accurately identify the tissue support and its contents using the displayed information, while if the tissue support identifier is verified too slowly it can be assumed that the technician may have become distracted and the identity of the tissue support is in doubt.

Preferably, the verification of the tissue support identifier is carried out between 1 second and 5 minutes after scanning of the tissue support at the identification reader wherein the system accepts the tissue support ID information and proceeds to allow the technician to print slides. More preferably, the verification of the tissue support is carried out between 1 second and 2 minutes after scanning of the tissue support at the identification reader. Even more preferably, the verification of the tissue support identifier is carried out between 1 second and 20 seconds after scanning of the tissue support at the identification reader.

This time interval may be, for example, preset or set by the user or lab manager. The time interval may be of fixed duration, i.e. not adjustable by the user. There may also be a signal, such as a waiting signal, that alerts the user shortly before the expiration of the time limit.

A decision system, such as a software program or electronic circuit, is used to control the operation of the printer and sectioning station. The decision system may receive inputs from the user verifying the identity of the sample, and from a timer, and may use these inputs to identify if the identification has occurred within a defined interval. The decision system may generate outputs that can be used to control the action of the printer, for example preventing application of the identifier to the tissue holder if the identity has not been verified correctly. The decision system may also send a signal to the sectioning station, which can be used to preventing or allow sectioning, for example by disengaging or engaging the drive to a microtome blade.

If the tissue support identity is verified by the method of placing the tissue support into the holding assembly, then consideration has to be made of the ability of the user to reorient the tissue support while sectioning a sample. This can be achieved in the following way; immediately the system detects that the tissue support is removed from the holding assembly it locks the printer and/or microtome from operating, as the support identifier is in doubt. If the system detects that a tissue support is placed into the holding assembly within a time-out interval of less than 5 seconds after removal, and preferably less than 1.5 seconds, then user is required to verify that the tissue support is still the same as before (i.e. the support has been reoriented, rather than replaced). If on the other hand the tissue support is removed from the holder for a period of time longer than the time-out interval, then system assumes that the identity of the tissue support is in doubt, and asks the user to re-enter the identity information (for example by re-scanning the tissue support identifier at the reader). Reorientation may be achieved manually by use of an adjust function, such as an adjust button which locks the ID until adjustment complete, or may be achieved automatically wherein a short timescale change locks the ID and requires the user to confirm that adjustment is complete.

If the tissue support identity cannot be verified (for example there is a discrepancy between the displayed information and the tissue support) then the technician can note the discrepancy and pass the tissue support to a supervisor to investigate the source of the error. Alternately, it may be possible for the supervisor or technician to override the error and continue processing the sample—such actions would be logged in the server database.

At step 105 the tissue support ID has been authenticated and the system is ready to process a given tissue support. On command, the slide dispenser feeds individual unprinted slides to the printer to be marked with identification information. The required information varies from lab to lab, but generally includes one or two unique identifiers, as well as information identifying the source of tissue, and may include information relating to the later processing of the slide, for example staining process and antibody information. The slide identification information may be derived from the information on the tissue support, from a link to the LIS, or from some other source. The system then prints the information to the slides as necessary, printing only the number of slides that the technician requires. In a preferred embodiment, the system only allows information to be printed that is relevant to the identified tissue support.

Suitable printers for use in the present invention include, but are not limited to, printers that print directly onto glass microscope slides, including printers that have been developed based on a variety of technologies—ink-jet (for example using UV or thermally curable inks), thermal transfer, impact printing using an ink-ribbon, or engraving or etching using a stylus or laser. Alternatively, the printer may print onto a label that can be applied either manually or automatically to the slide. The term printing is also intended to encompass the act of writing data to an RFID tag which may be affixed to or embedded into the slide, and writing data to media such as other electronic or magnetic memory devices or e-ink. Such alternate media may also be supplied in the form of a label that can be printed with human readable data. The printer may be incorporated into the microtome, or may be separate from it.

Activation of the slide dispenser may be automatic after a given tissue support identification is authenticated (e.g. the ID is read and the tissue support is placed into the holding assembly within the appropriate timeframe), or it may be under the manual control of the technician. The number of slides prepared for a given tissue support may be determined from an item in the tissue support information or it may be manually entered or altered by a technician. If more than one slide is required for the given tissue support, the printing of the next slide may be triggered by the removal of the first identified slide from the slide dispenser, or it may be under the control of the technician. Alternatively, printing of slides may be activated by the user pressing an appropriate button, or by using a graphical user interface (GUI) and slides printed by the user manually entering inputs—this may be achieved in a variety of ways, for example pressing buttons on the device, or clicking on a representation of the slide on the display screen. Printing of slides may be prevented if the tissue support is removed from the holding assembly prior to the slide being printed.

In a preferred embodiment, the slide dispenser may be provided with a volume or level sensor (not shown) for sensing when the slide dispenser is running low on slides. This sensor may cause a warning light or other suitable indicator to notify the technician to replenish the slides. In a preferred embodiment the printer may access a number of slide dispenser mechanisms that may be loaded with, for example, different colours or types of slides. Selection of the slide colour or type may be determined from an item in the tissue support information, or from the LIS; it may be inferred from laboratory rules determining the handling of certain types of tissue samples, or may be under the manual control of the technician.

The technician may override the default values for the number or colour of slides to be printed. For example, a technician may identify that an additional slide is required for a sample being sectioned. Alternately, the technician may break a slide prior to picking up a tissue section, in which case the technician would need to reprint an existing slide. The system can be designed to allow for version control on slides, such that even when a broken slide is reprinted, it still has a unique identifier. Many coding systems could be used for this, an example being that if the slide identifier for the broken slide was A123, then the replacement slide could be numbered A123.1 to identify that it is a replacement for slide A123. A similar coding system could be used to identify a replacement that was generated for a slide that was broken when tissue was on it—i.e. to identify that both the slide and tissue section are being replaced.

The printed slides may either be manually picked-up as they exit the slide dispenser, or an accumulating extension can be added to the exit conveyor to increase capacity. In a preferred embodiment, only a single slide is available to the technician at any time.

In step 106 the tissue is sectioned. After loading of the tissue support into the holding assembly thin sections of tissue are cut, and for paraffin-embedded tissues the sections are generally floated onto a water bath to remove wrinkles.

Figure 7:
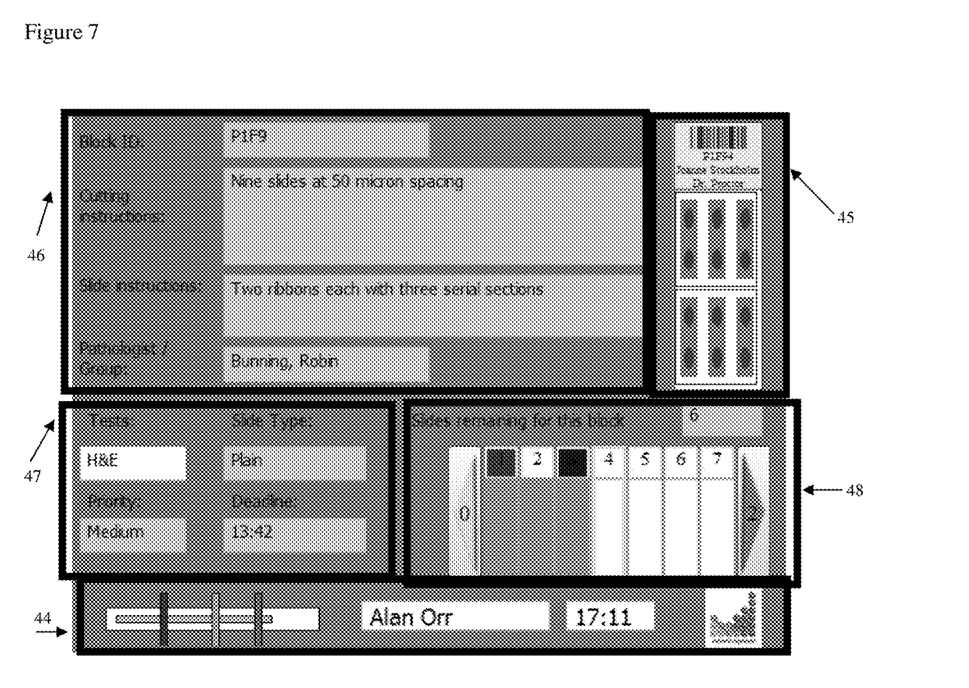
FIG. 7 shows an example of a tissue holder identification information that may be displayed to the user.

In step 107 the tissue sections are then mounted onto tissue holders (such as a glass microscope slide from step 105) that have been identified as relating to the tissue support. With paraffin-embedded tissues this generally involves using the microscope slide to remove sections from a water bath. Often more than one section is placed onto a single slide, and in a preferred embodiment, in step 104*a* instructions and/or images relating to the way in which sections are to be cut and positioned on the slide are shown on the display device along with the identification information (an example of data that may be displayed at step 104*a* is shown in FIG. 7). In a cytology or haematology environment step 107 would relate to the deposition of a thin layer of cells onto on a microscope slide, for example using a smear or touch preparation.

In step 108 the user indicates to the system that the sectioning of a tissue support is complete. This may be when the tissue support is removed from the holding mechanism, or may be some other form, for example the user pushing a button on the device, scanning a further tissue support or by manual data entry such as the user entering the identification information for another tissue support. In a preferred embodiment, when the user indicates to the system that sectioning is complete, this causes the data that was displayed at stage 103 and 104*a* to be removed from display, and preferably prevents the printer from printing new slides, and prevents the microtome mechanism from operating until another support ID is verified.

In step 109 the tissue support can now be filed, as it is not required for cross-referencing with the slides. The slides produced according to the present invention may then be processed by staining at step 110, coverslipping at step 111 and sorted at step 112 for distribution to, for example, a pathologist for analysis and/or diagnosis at step 113.

Figure 2:
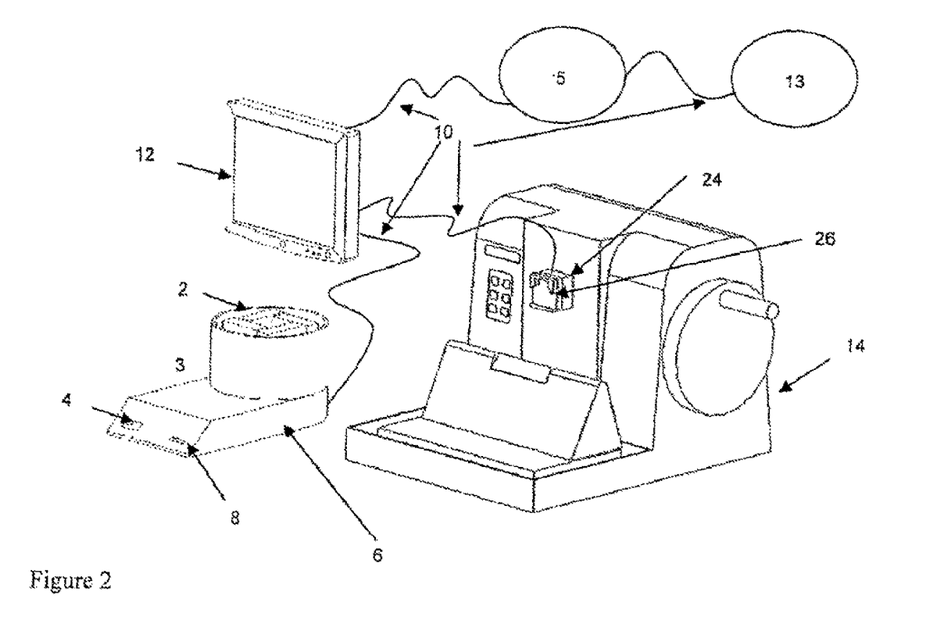
FIG. 2 is a depiction of a typical configuration of the invention.
Figure 3:
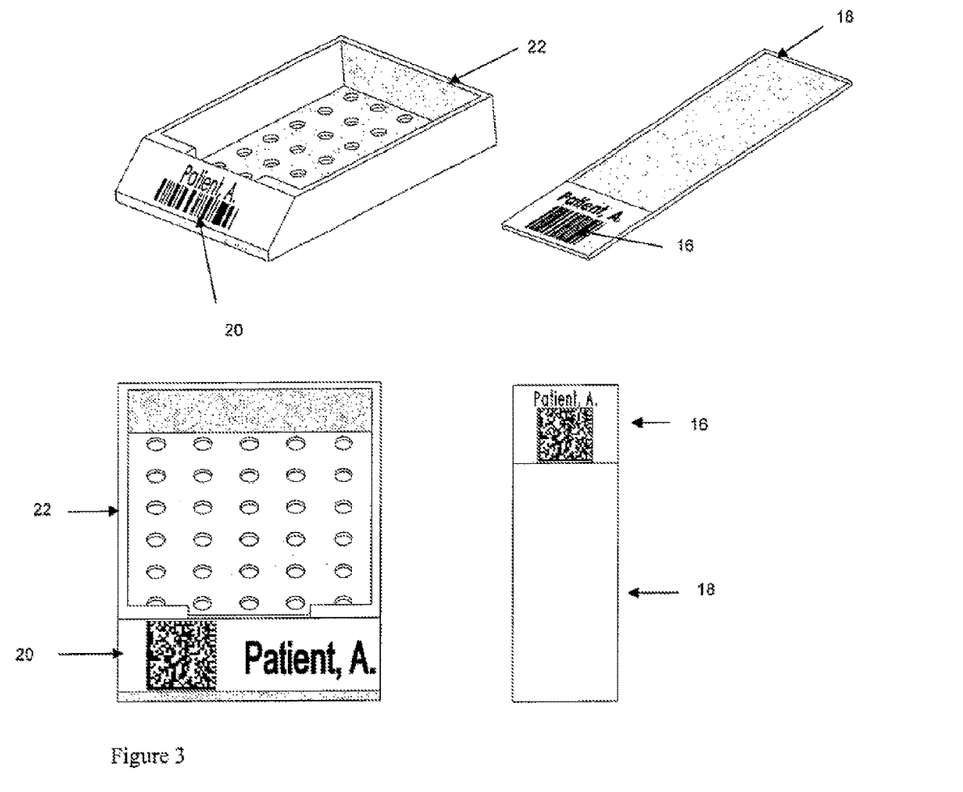
FIG. 3 shows typical identification marks on slides and cassettes.

Referring to FIGS. 2 and 3, the device 3 according to a preferred embodiment of the present invention comprises slide dispenser 2 and tissue support reader 4 (e.g. bar-code reader, OCR reader, RFID reader and the like) a printer 6 and display screen 12. In a preferred embodiment the device is linked to a Lab Information System 13 via a server 5 that handles the communication between the LIS and one or more devices, and may be arranged to contain information relating to the Laboratory rules for handling tissue samples. The device 3 may be freestanding as shown in FIG. 2, may be connected to the microtome (not shown) or may be integral with the microtome (not shown). The display screen 12 may be integral to the device (not shown).

The tissue support reader 4 is preferably located in close proximity to the microtome station, and may be integral with the microtome station. Alternatively, the tissue support reader 4 may be a hand-held device such as a scanner (not shown). A tissue support identifier 20 is associated with the tissue support 22. The tissue support identifier 20 may be, for example, attached to, be integral with, or attached via a carrier to the tissue support 22. The tissue support identifier 20 is shown as a barcode, but it will be appreciated that the identifier 20 may be any suitable markings or devices including, but not limited to, any combination of hand written identifiers, printed text, a bar code (1, 2 or 3 dimensional), data glyphs, Optical Character Recognition (OCR) code, Radio Frequency Identification (RFID) tags and e-ink.

Slides may be manually loaded into slide dispenser 2. Slide dispenser 2 may be a vertical canister mounted directly over printer 6. The slide dispenser 2 may have more than one container for slides 18 (for illustration purposes four are shown in FIG. 2), which may contain different types or colours of slides. Alternately, slides may be entered into a dispenser in pre-loaded cartridges that have already been filled with slides. Slide dispenser 2 releases one slide 18 for each print cycle and printer 6 prints slide identifier 16 on slide 18. The slide identifier 16 may be, for example, attached to, be integral with, or attached via a carrier to the slide 18. The slide identifier 16 is shown as a barcode, but could be any suitable marking or device including, but not limited to any combination of printed text, a barcode (1,2 or 3 dimensional), data glyphs, OCR code, RFID tags and e-ink. The slide identifier 16 need not be of the same form as the tissue support identifier 20.

Printer 6 transfers ID information to the slide identifier 16 by, for example, labelling/direct printing/writing to an RFID chip in the slide etc. based on the information scanned from the tissue support identifier 20. In addition, the slide identifier 16 may be coded with information regarding the tissue sample, and may further include information regarding the sample slice sequence where several sample slices are taken (e.g., "slice 1 of 3"), and may further include processing instructions for the slide 18. Furthermore, information can also be noted on slide—for example, if a slide containing tissue is broken, then an additional slide can be printed, and a note can be made that the slide is out of order (e.g. "slide 4 of 3, replaces slide 2"). Information printed on the slide may also include such information as a protocol for staining. The microscope slide 18 exits printer 6 at slide exit 8.

It will be appreciated that the identifier 20 on the tissue support 22 may be different in form to the identification information 16 assigned to the tissue holder 18, for example, in a situation where the tissue support 22 originates in an outside laboratory that uses a different identification system, such as a different numbering or labelling system. Preferably, where the identifier 20 on the tissue support 22 is different to the identification information assigned to the tissue holder 18, a link is provided, such as in the LIS, that correlates the identifier 20 on the tissue support 22 with the identification information 16 assigned to the tissue holder 18.

The printer 6 interfaces via a communication system 10 with a display screen 12, and optionally a sensor 24 located in the microtome 14, and preferably is provided with a communication path to a server 5 and the Laboratory Information System (LIS) 13. After scanning the tissue support identifier 20 using the tissue support reader 4, information relating to the tissue and the tissue support 22 may be displayed as a visible read-out for the technician on a display screen 12. Display screen 12 may be any suitable display means, including flat-panel displays, CRTs, LCD displays, projectors and touch-screens, and may be, for example, part of a flat-panel or handheld computer. In one embodiment, a touch-screen is used to display information and to simultaneously serve as an input means. Other input means, such as scanners (barcode, RFID), keyboards, keypad; foot controls, joysticks etc., may also be used. The display may be integral to the printer 6, and further the printer 6 may additionally be integrated into the microtome 14.

In an embodiment, the device 3 applies material and/or data comprising a unique identifier, such as a pre-printed label or RFID tag, for placement onto slides whereupon the unique identifier is correlated to information in an LIS, or information held on a database resident on an automated staining device such as a Bondmax instrument sold by the applicant. This approach provides reduced complexity and cost as no printer or writer is required.

In a preferred embodiment, the printer 6 creates human and machine-readable markings onto the slide 18 using an inkjet, direct thermal or thermal transfer mechanism. Preferably, an ink is used that provides that the markings are resistant to the chemicals used within histology processing. Alternately, a surface preparation may be applied to the slide frosting prior to printing to ensure a chemical bond between the ink and slide—in the case of thermal transfer inks this coating may be formed using standard label coating media such as PET, PVC, PVA, BOPP, Kimdura, polyimide or other suitable materials known in the art. In an embodiment, the ink comprises a standard ink, e.g. a water, solvent, wax, resin or wax/resin ink, and the markings are protected by the addition of a chemical resistant coating over the top of the ink. Preferably, the coating is optically transparent, and may be formed by depositing a suitable coating followed by rapid curing by, for example, heat, UV, infra-red (IR), e-beam or a combination of these. Alternately, printing may be made onto a label that is applied to the slide. In a preferred embodiment the printing is carried out by thermal transfer printing a mirror-image of the desired information onto the back surface of a transparent label material. This back surface is then laminated onto the slide such that the ink is protected from the chemical environment by the transparent surface.

It is preferred to allow the technician to modify system parameters, for example by operating controls on the printer 6 or the display screen 12. For instance, the technician may have the ability to modify the number of microscope slides 18 printed. The invention also allows the technician to make real-time adjustments to the data relating to the slide and slide identification as stored within a database (for example the LIS, a database on the server 5, or a database on a staining instrument such as the BondMax instrument sold by the applicant), so that teat-time information is available for later slide processing.

In a preferred embodiment, the printer 6 of the present invention interlocks to the identified tissue support 22 and to the Laboratory Information System (LIS) 13 such that only information regarding the currently identified tissue support 22 is available to the technician. The user validates the information against the tissue support 22, and positions the tissue support 22 into the chuck 26 in the microtome 14 for sectioning.

Preferably, following clamping of the tissue support 22 in the microtome chuck 26, the presence of the tissue support 20 in the microtome chuck 26 is detected by a sensor 24, such as an optical, mechanical, magnetic etc. sensor.

The time interval between the user entering the tissue support identifier 20 into the system (for example by scanning at the reader 4) and validating the information (for example validation may be indicated by positioning the tissue support in the chuck 26) is used to ensure that the data is correct. If the tissue support ID is not verified within a predetermined timeframe, the printer 6 and/or microtome 14 will lock until a tissue support ID is entered again. In this way, printing of slides and/or processing of the block may be stopped automatically if the tissue support ID is in question.

Preferably, the tissue support ID 20 is verified between 1 second and 5 minutes after entering of the tissue support identifier 20 into the system, whereupon the system accepts the tissue support ID 20 and allows the operator to print a slide 18. More preferably, the tissue support ID 20 is verified between 1 second and 2 minutes after scanning of the tissue support ID 20 at the tissue support identification reader 4. Even more preferably, the tissue support ID 20 is verified between 1 second and 20 seconds after scanning of the tissue support ID 20 at the tissue support reader 4. The time interval may be, for example, preset or set by the user or lab manager.

The tissue support ID 20 must be verified before it can be processed. In the event a tissue support's identification cannot be read, or the verification is in doubt, then the processing sequence may be stopped automatically. In another embodiment, the technician or a supervisor may be able to correct any incorrect data, or override the system and continue the process despite the tissue support identification error.

In a preferred embodiment, the printing of the first slide is triggered by placing of the tissue support 22 into the microtome chuck 26 within a pre-determined time interval of the tissue support ID 20 having been scanned at the tissue support reader 4. Once the first slide 18 has been printed, it is presented to the technician at the slide output 8. If more than one slide is required for the tissue support 22, then it is preferred that removal of the first slide from the slide output 8 triggers the printing of the next slide relating to that tissue support, provided that the tissue support 22 has not subsequently been removed from the microtome chuck 26. This process is repeated until all slides relating to the tissue support 22 are printed. It is also possible that the slide printer 6 has a collection mechanism at the slide output, and that once printing is triggered all slides relating to the block are printed.

Once the tissue is sectioned, it is generally floated on water. The technician then brings an identified tissue holder 18, such as a microscope slide, up under the portion of the floating tissue section and captures the full tissue specimen. The slide 18 with sample section is then set aside for drying, staining and evaluation, or for various molecular, cytological or histochemical analysis.

Figure 4:
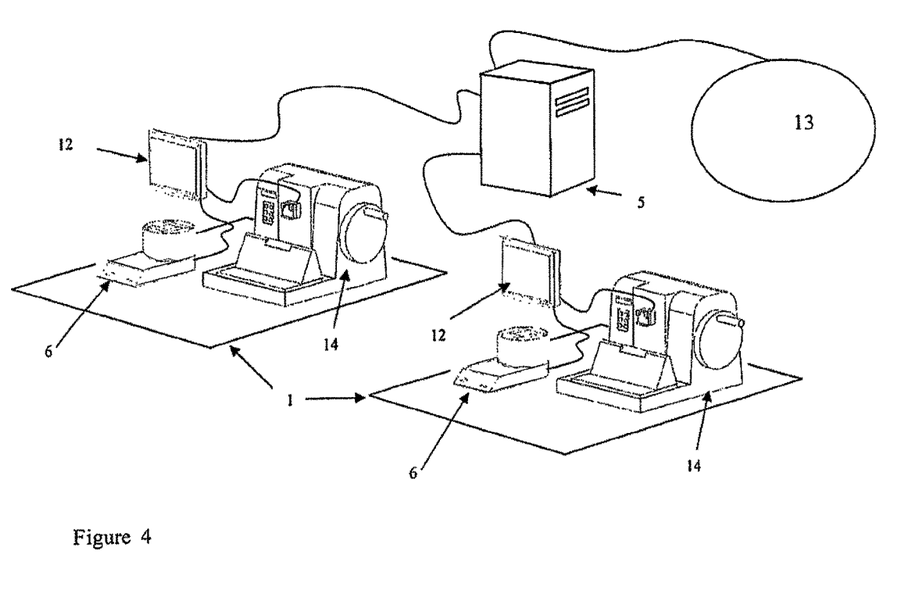
FIG. 4 is a schematic diagram showing the connection of multiple identification devices to a server and optionally to the Laboratory Information System (LIS) via a server.

One preferred embodiment of the connection to the Laboratory Information System is shown in FIG. 4. Here, a communications link connects identification systems 1, to a server computer 5, which has a separate communications link to the LIS 13. In the drawing two identification systems, 1, are shown, but more may be connected as necessary depending on the size of the laboratory. The server computer 5, has a random-access local storage device, e.g. a hard disk drive (not shown) that provides local storage of information remote from the LIS 13.

The local storage allows a variety of different forms of connection to the LIS 13 to be permitted (e.g. store-and-forward, direct connection, connection via file transfer). The local storage also allows the server to store programs and information. The server may be used to modify the data from the LIS before sending out data for display at the devices. For example, on installation in a laboratory the server may be programmed with laboratory rules that determine a variety of information relating to the tissue and the identified tissue support. For example, the number of slides, cutting instructions and required tests may be determined from the tissue type, but may not be stored in the LIS directly. By using data relating to the specific handling of tissues by an individual laboratory, the server may be able to present more detailed information to the user of the device than is available directly from the LIS.

The server may directly control the display devices 12, of the identification systems 1, or alternately the display device 12, may be computer terminals such as flat panel PCs, in which case a computer programme running on the display device 12, may connect to the server 5, as required to access its information. By having data stored on a central server 5, the identification systems 1 can access data relating to tissue supports and tissue holders that have been used or created on other identification systems, for example showing if a cassette has already been sectioned on another system.

In one embodiment, the local storage server 5 may not connect to an external LIS 13—this configuration may be used, for example, when sufficient information is available in the support identifier 22 and the local storage server 5 to at least enable the automatic generation of the slide identifier 16, and the generation of the displayed data for support verification. In another embodiment the identification systems are linked directly to the LIS and no server is used, while in still a further embodiment the identification systems are used in isolation from each other.

The local storage server 5 may be used to track the usage of the identification systems 1, such that all user activities are logged (for example, user log-ons, cassette identification, slide printing activities, maintenance activities, more/less slides used or if slides are broken). This may allow the generation of reports for quality control or other purposes.

Figure 5:
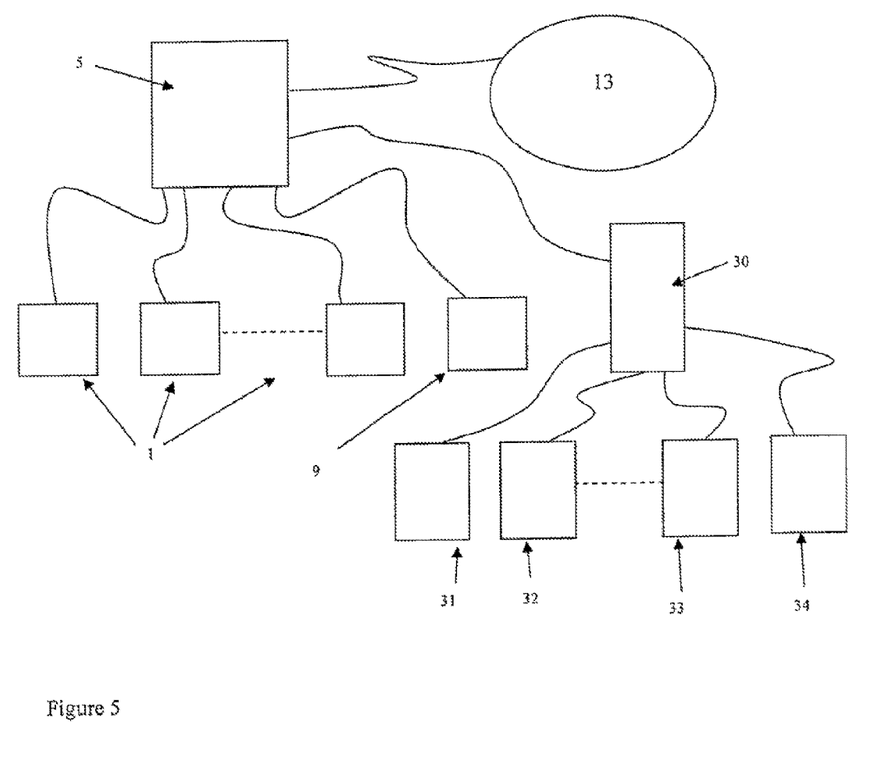
FIG. 5 is a schematic diagram showing the connection of identification devices to other automated apparatus.

The local storage on the server 5, also permits a further extension of this system, as shown schematically in FIG. 5. Here a number of identification systems 1 are connected to a server computer 5 that has local storage of information. In addition, data terminals 9, can also access the server. The server computer 5 is connected to a further computer system 30, and may also be connected to the LIS 13. The computer system 30 controls a number of other pieces of automated laboratory equipment, which may include, for example an IHC stainer 31, H&E stainer 32, coverslipper 33, and slide router 34, although further equipment may be added as necessary, and more than one of each type is permitted. The computer system 30 and the server 5, may, in some configurations, be the same machine, or there may be more than one computer system 30 controlling other equipment.

The data terminals 9 may be used to access the server 5 or LIS 13, for example, to add instructions. These may be used, for example, by a pathologist to request additional testing on a tissue sample, or by a supervisor to update records or print reports on the activity of the identification systems. This also provides an input for additional information such as logging damaged blocks or blocks requiring reprocessing.

Linking of systems together via a database that logs use data from a variety of sections further provides information on whether a block has been sectioned previously.

Traditionally slides are relabelled before being placed onto an automated stainer, as the stainer cannot read the data on the slide. With the system shown in FIG. 5, data relating to the machine-readable identifier on the slide is accessible to the stainers 31 and 32, the coverslipper 33 and to the slide router 34 by connection through the computer system 30. The stainers can therefore access the information regarding which staining protocol is to be run by accessing the information from the server 5 via the computer system 30. The slide router is an additional machine that can collect the slides from the microtome workbench. By reading the machine readable identification on the slide and linking this to the information stored in the server 5, the slide router can automatically direct slides through to the correct machine, e.g. the IHC stainer 31, the H&E stainer 32 or the coverslipper 33. The slide router 34, stainers 31 and 32 and coverslipper, 33 may in some cases all be part of the one machine.

Information regarding the tests to be conducted on a particular slide can be used to identify the path that the slide should take through the laboratory (e.g. the stainer that it should be placed on) and can be used by later automated processing steps as indicated in FIG. 5.

An example of the data that might be made available on the display device 12 is shown in FIGS. 6 and 7. It should be noted that this is just an example of the data that can be presented, and it is possible to display all data that can be accessed for the tissue support and tissue holders, e.g. data from the server or LIS, or that can be inferred from the LIS data, server data and the laboratory rules (for example, block layout may not be stored in the LIS, but laboratory embedding rules may dictate a particular layout which may be coded into the display system). Data is presented to the technician after the cassette has been scanned.

In FIG. 6 data relating to the tissue support is shown, including at 41 a graphical representation of the tissues embedded in the cassette. Data relating to the tissue type, grossing description and sectioning instructions are shown at 42. Data relating to associated tissue supports is shown at 43, and user log-in data are shown at 44.

In FIG. 7, data relating to the tissue holder is shown. At 45, a graphical representation of the slide to be generated is given, indicating tissue ribbons and orientation, plus label data to be printed. Shown at 46 is data relating to the tissue support from which the slides derive, including identifier number, cutting instructions for the block and the pathologist who will be reporting on the block. At 47 is shown data relating to the tests to be performed and slide type to use for this particular slide, while at 48 is shown data relating to other slides to be generated for slides cut from this particular tissue support.

By using the information presented in FIG. 6 the technician can readily verify that the embedded tissues in the tissue support that they have just scanned are indeed the tissues to which the identifier 20 on the tissue support relates. The information presented in FIG. 7 allows the user to readily determine what is needed when generating slides from an identified tissue support. The sectioning instructions shown at 46 can be used by the technician in preparation of the sectioned tissues—special instructions may be used for example if the pathologist has requested additional testing. The graphical representation of the slide at 45 can be used as a reminder of the slide layout required, and also to check that the printed identification information is correct according to the required information from the LIS system.

While the invention has been described in connection with preferred embodiments and examples, it will be understood by those skilled in the art that other variations and modifications of the preferred embodiments described above may be made without departing from the scope of the invention. Other embodiments will be apparent to those skilled in the art from a consideration of the specification or practice of the invention disclosed herein. It is intended that the specification is considered as exemplary only, with the true scope and spirit of the invention being indicated by the following claims.

"Comprises/comprising" when used in this specification is taken to specify the presence of stated features, integers, steps or components but does not preclude the presence or addition of one or more other features, integers, steps, components or groups thereof."

What is claimed is:

1. A pathology tissue identification method comprising:
   reading, by a reader, identification information from a tissue support input into a microtome;
   receiving, by a computer, the read identification information, the computer is connected to the microtome via a communication system;
   outputting, on a screen of the computer, data related to the received identification information;
   determining, by the computer, whether other tissue support is being hold by a holding assembly connected to the computer via the communication system based on information detected by the holding assembly and communication via the communication system to the computer;
   wherein:
      in response to the determining yielding that no other tissue support is detected in the holding assembly, processing in the microtome, based on the output data, a tissue on the tissue support,
      in response to the determining yielding that said other tissue support is being identified in the holding assembly, outputting, on the screen of the computer, an error indicator, and
      said determining if the other tissue support is being concurrently identified in the holding assembly comprises determining that the holding assembly holds said other tissue support that is inconsistent with the identification information currently stored in an identification computer system.

2. The method of claim 1, wherein the output data comprises a number of tissue holders needed to perform the pathology tests, information specific to the tissue support, and information specific to the tissue holders.

3. The method of claim 2, wherein the information specific to the tissue support comprises type of tissue, cutting instruction and grossing description, and
   wherein the information specific to the tissue holders comprises a number of tissue holders already prepared and a remaining number of tissue holders that are to be prepared, test instructions for each of the tissue holders, type of tissue holder, and type of test to perform for each respective tissue holder.

4. The method of claim 1, wherein the output data comprises at least one selected from among: a number and status of related tissue supports, a type and a number of tissue pieces embedded in the tissue support, images and descriptions of the tissue provided in the tissue support, patient data, and instructions for cutting the tissue provided on the tissue support.

5. The method of claim 1, wherein the output data is obtained from a remote laboratory information system or encoded along with the identification information.

6. The method of claim 1, further comprising:
   analyzing, by the computer, the received identification information and applying, by the computer, a predetermined criteria based on the analyzed identification information to determine the output data.

7. The method of claim 6, wherein the output data comprises instructions for said processing, which is based on the received tissue support identification information.

8. The method of claim 1, wherein the identification information comprises type of tissue provided on the received tissue support identification information and wherein based on the type of tissue, the output data is determined and comprises number of slices to prepare from the tissue provided on the tissue support.

9. The method of claim 8, wherein the output data further comprises the number of slices to be placed on each of a plurality of tissue holders.

10. The method of claim 1, further comprising detecting the tissue support at the certain station within a predetermined period of time, wherein the processing is triggered by the detected tissue support.

11. A tissue pathology processing method comprising:
    receiving, by a holding assembly, a tissue on a tissue support to hold the tissue sample for sectioning;
    receiving, by a computer connected to the holding assembly via a communication system, identification information for the tissue support;
    outputting, on a screen of the computer, data related to the received identification information;
    automatically determining, by the computer, that no other tissue support is currently being identified at the holding assembly tied to the computer; and
    in response to said determining indicating that no other tissue support is currently being identified at the holding assembly, automatically releasing a plurality of tissue holders from a dispenser and generating identification information for a plurality of tissue holders to hold the tissue and attaching the generated identification information onto each of the released plurality of tissue holders; and
    in response to said determining indicating that at least one other tissue support is currently being identified at the holding assembly, the computer controlling the holding assembly to not release of the plurality of tissue holders from the dispenser and output an error on a display of the computer, and
    sectioning, by the microtome, based on the output data, the tissue on the tissue support and placing each piece of the tissue onto a respective tissue holder with the attached identification information from among the plurality of tissue holders.

12. The method of claim 11, further comprising:
    receiving the tissue support in the holding assembly after performing repositioning of the tissue support, if the tissue support is received after a predetermined period of time, re-executing the receiving of the input identification information, the outputting, and the determining, and if the tissue support is received within the predetermined period of time, automatically continuing processing of the tissue support without repeating said verification.

13. A system of processing a tissue provided on a tissue support comprising:
a microtome having a holding assembly to hold the tissue support configured to hold a tissue and a sensor configured to detect the tissue support in the holding assembly; and
an apparatus comprising:
a reader which reads identification information for the tissue support in the holding assembly;
a display which displays data related to the read identification information; and
a processor which verifies that no other tissue support is currently being hold by the holding assembly based on an output from the sensor, and which generates identification information for a plurality of tissue holders, based on the displayed data if no errors are detected during said verifying,
wherein the processor performs the verification by determining if said other tissue support is currently being identified at the holding assembly by the sensor,
wherein if the processor determines that said other tissue support is currently being identified at the holding assembly by the sensor, the processor controls the display to output an error indicator and halts the processing of the tissue support by the microtome,
wherein the processor provides instructions for performing pathology tests on the tissue and provides instructions for holding the tissue support with the tissue in the holding assembly during processing,
wherein the processor further determines if the other tissue support is present in the holding assembly based on identification information currently stored in the apparatus as active,
wherein the displayed data comprises a number of tissue holders needed to perform the pathology tests, information specific to the tissue support, and information specific to the tissue holders,
wherein the information specific to the tissue support comprises type of tissue, cutting instruction and grossing description,
wherein the information specific to the tissue holders comprises a number of tissue holders already prepared and a remaining number of tissue holders that are to be prepared, test instructions for each of the tissue holders, type of tissue holder, and type of test to perform for each respective tissue holder,
wherein the processor prepares instructions to attach the identification information to each of a plurality of tissue holders,
wherein the processor prepares instructions to cut the tissue provided on the tissue support into a plurality of slices,
wherein the processor prepares instructions to receive at least two of the plurality of slices placed onto respective prepared tissue holders, and
wherein the processor prepares instructions to perform a respective pathology test on each of the received slices.

14. The system of claim 13, further comprising: a speaker which outputs acoustic notifications, wherein the processor output the error indicator to the speaker which provides an acoustic notification representing the error indicator.

15. The system of claim 13, wherein the display data comprises at least one selected from among: a number and status of related tissue supports, a type and a number of tissue pieces embedded in the tissue support, images and descriptions of the tissue provided in the tissue support, patient data, and instructions for cutting the tissue provided on the tissue support.

16. The system of claim 13, wherein the displayed data is obtained by the processor from a remote laboratory information system or encoded along with the identification information.

17. The system of claim 13, further comprising:
analyzing, by the processor, the received tissue support identification information and applying, by the processor, a predetermined criteria based on the analyzed received tissue support identification information to determine the displayed data.

18. The system of claim 17, wherein the displayed data comprises instructions for processing tissue provided on the tissue support based on the received tissue support identification information.

19. The system of claim 13, wherein the received tissue support identification information comprises type of tissue provided on the received tissue support identification information and wherein based on the type of tissue, the displayed data is determined and comprises number of slices to prepare from the tissue provided on the tissue support.

20. The system of claim 19, wherein the displayed data further comprises the number of slices to be placed on each of a plurality of tissue holders.

21. The system of claim 13, wherein the sensor is configured to detect that the tissue support is in the holding assembly within a predetermined period of time, wherein further processing of a tissue is triggered by the verified tissue support detected by the sensor.

22. The system of claim 13, further comprising:
a sensor which detects the tissue support in a holding assembly after performing repositioning of the tissue support,
wherein if the tissue support is received after a predetermined period of time, re-executing the receiving of the input identification information, the outputting, and the verifying, and
wherein if the tissue support is received within the predetermined period of time, the processor automatically continues processing of the tissue support without repeating said verification.

23. A method of processing a tissue provided on a tissue support comprising:
reading identification information from the tissue support input into a microtome;
receiving, by a computer, the read identification information;
outputting, on a screen of the computer, data related to the received identification information;
automatically verifying, by the computer, that no other tissue support is currently being identified at a holding assembly connected to the computer;
processing in the microtome, based on the output data, the tissue on the tissue support if no errors are detected during said verifying;
analyzing, by the computer, the received identification information and applying, by the computer, a predetermined criteria based on the analyzed identification information to determine the output data, wherein the output data comprises instructions for said processing, which is based on the received tissue support identification information;
wherein the verifying comprises determining if said other tissue support is currently being identified at the holding assembly,
wherein, in response to the determining indicating that said other tissue support is currently being identified at the holding assembly, outputting an error indicator, and
wherein said determining if the other tissue support is being concurrently identified comprises determining that the holding assembly holds said other tissue support that is inconsistent with the identification information currently stored in an identification computer system.

* * * * *